United States Patent
Sakakibara et al.

(10) Patent No.: US 7,326,558 B2
(45) Date of Patent: Feb. 5, 2008

(54) PROCESS FOR TREATING SPIRULINA

(75) Inventors: Masaki Sakakibara, Chiba (JP);
Yoshitsugu Fukuda, Ichihara (JP);
Akiko Sekiya, Kisarazu (JP); Hideji Nishihashi, Sakura (JP); Tomohiro Hirahashi, Ichihara (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 0 days.

(21) Appl. No.: 11/080,681

(22) Filed: Mar. 16, 2005

(65) Prior Publication Data
US 2006/0210545 A1    Sep. 21, 2006

(51) Int. Cl.
*C12N 1/12*    (2006.01)

(52) U.S. Cl. .............................. 435/257.1; 435/257.3; 435/252.9

(58) Field of Classification Search ............. 435/257.1, 435/257.3, 252.9
See application file for complete search history.

(56) References Cited

U.S. PATENT DOCUMENTS 5,276,977 A * 1/1994 Cysewski ................... 34/371

FOREIGN PATENT DOCUMENTS

| JP | 63-157963 | 6/1988 |
| JP | 7-289201 | 11/1995 |

OTHER PUBLICATIONS

Varga L. et al. "Influence of a *Spirulina platensis* biomass on the microflora of fermented ABT milks during storage (R1)", J. Dairy Sci., 2002, 85(5): 1031-1038. entire document.*
Conway PL. "Prebiotics and human health: the state-of-the-art and future perspectives"—Review article, Scandinavian Journal of Nutrition, 2001, 45: 13-21. entire document.*
Belay A. "The potential application of Spirulina (Arthrospira) as a nutritional and therapeutic supplement in health management"—Review article. The Journal of the American Nutraceutical Association, 2002, 5(2): 27-48. entire document.*
Tserovska L. et al. "Identification of lactic acid bacteria isolated from Katyk, goat's milk and cheese". Journal of Culture Collections, 2000-2002, 3: 48-52. entire document.*
Bioprophyl GmBH, "Spirulina-platensis: A micro alga of a special kind", at the web—http://www.bioprophyl.biz/catalog/spirulina.shtml. pp. 1-5.*
Gyenis B. et al. Use of powdered microalgae to stimulate acid production and growth of . . . in milk, Poster presentation, Jul. 27, 2004, Abst. # T3, J. Anim. Sci. vol. 82, Suppl. 1/ J. Dairy Sci. vol. 87, Suppl. 1/Poult. Sci. vol. 83, Suppl. 1, pp. 1-4.*

* cited by examiner

*Primary Examiner*—Sandra E. Saucier
*Assistant Examiner*—Satyendra K. Singh
(74) *Attorney, Agent, or Firm*—Edwards Angell Palmer & Dodge LLP

(57) ABSTRACT

The treatment of spirulina by a process which includes placing spirulina that has not been previously heat-sterilized, lactic acid bacteria and sugar in water, then culturing the lactic acid bacteria provides treated spirulina in which the distinctive taste and odor of spirulina are minimized, in which active ingredients such as phycocyanin remain intact, and which contains a reduced level of bacteria other than lactic acid bacteria.

10 Claims, No Drawings

PROCESS FOR TREATING SPIRULINA

BACKGROUND OF THE INVENTION

1. Field of the Invention

The present invention relates to a process for treating spirulina. The distinctive odor and taste of spirulina are minimized in treated spirulina obtained by the inventive process, making the treated spirulina highly suitable for use in products such as beverages and foods.

2. Description of Related Art

Spirulina is a food product which is rich both in nutrients characteristic of green and yellow vegetables and nutrients inherent to itself, and which enables nutrients that tend to be underrepresented in a normal diet to be easily ingested. Spirulina is generally supplied in the form of a dry powder (bulk spirulina powder). Bulk spirulina powder is typically manufactured by harvesting wet algae which has been industrially grown and produced on a large scale in an artificial outdoor pond designed for that purpose, then concentrating, washing and drying the harvested algae as needed. However, because spirulina powder produced by such a method has a characteristic odor and taste, within the food industry, it is used only in a very limited number of products, primarily health foods and specialty feeds for animals.

Methods for reducing the characteristic odor and taste of spirulina include the production process described in JP-A 7-289201, which involves adding a tea leaf extract to a cultured spirulina suspension, then drying the spirulina to a powder. However, the spirulina powder obtained by this prior-art production process continues to retain the odor and taste characteristic of spirulina.

In the food products industry in general, to maintain proper hygiene, there exists a desire to further reducing the number of undesirable bacteria such as *Escherichia coli* in food. For example, JP-A 63-157963 discloses a method for lowering the level of foreign bacteria in food that involves the high-temperature sterilization of an aqueous suspension composed primarily of chlorella prior to cultivating the chlorella. This prior-art publication describes an example in which chlorella, nonfat dried milk and lecithin were dispersed in distilled water, and the dispersion was passed through a high-temperature sterilizer and sterilized at about 130° C. A bacterial culture was then added and fermentation was carried out to a predetermined acidity, following which the fermented material was cooled to a temperature at which fermentation ceases, giving a food product. Although the level of foreign bacteria in the food product obtained by such a process is reduced, because the process includes treatment at a high temperature, desirable active ingredients within the food are lost.

Hence, spirulina suspensions and powders thereof which have little of the odor and taste characteristic of spirulina, contain few foreign bacteria, and retain without loss active ingredients that are desirable in food products have not hitherto been achieved.

SUMMARY OF THE INVENTION

It is therefore an object of the invention is to provide a spirulina treatment process which is capable of producing treated spirulina that has little of the odor and taste characteristic of spirulina, contains few foreign bacteria, and retains the active ingredients.

By mixing spirulina with lactic acid bacteria and culturing the lactic acid bacteria, we have found it possible to decrease the characteristic spirulina odor and taste, lower the level of foreign bacteria by the antibacterial action of substances such as organic acids (e.g., lactic acid and acetic acid) and bacteriocin produced during culturing of the lactic acid bacteria, and impart beneficial lactic acid bacteria and metabolites thereof to spirulina or spirulina-derived components while at the same time retaining the active ingredients of spirulina. Treated spirulina obtained in this way is readily amenable for use in health foods and other food-related products.

Accordingly, the present invention provides a process for treating spirulina, which process includes the steps of placing spirulina that has not been previously heated and sterilized, lactic acid bacteria and sugar in water, then culturing the lactic acid bacteria. The spirulina is used in an amount of preferably 1 to 20 parts by weight per 100 parts by weight of the spirulina, lactic acid bacteria and water combined. The number of lactic acid bacteria at the start of lactic acid bacteria cultivation is preferably from $1 \times 10^6$ to $1 \times 10^9$ cells per gram of spirulina (solids basis), in which case the lactic acid bacteria are typically cultured at a pH of 6 to 8 for a period of 8 to 24 hours. The spirulina used may be spirulina powder or live spirulina. The lactic acid bacteria used are preferably lactic acid bacteria which belong to a genus such as *Pediococcus* or *Lactobacillus*. The sugar is used in an amount of preferably 0.5 to 20 parts by weight per 100 parts by weight of the spirulina, lactic acid bacteria, water and sugar combined. Preferred use may be made of galactooligosaccharide as the sugar.

The inventive treatment process provides treated spirulina in which the characteristic spirulina taste and odor are minimized, in which active ingredients such as phycocyanin remain intact, and which contains a reduced level of bacteria other than lactic acid bacteria.

DETAILED DESCRIPTION OF THE INVENTION

The invention is described more fully below.

"Spirulina," as used herein, refers to tiny spiral algae of the class Cyanophyceae, order Nostocales, family Oscillatoria and genus *Spirulina*. Examples include *Spirulina platensis, Spirulina maxima, Spirulina geitleri, Spirulina siamese, Spirulina major, Spirulina subsalsa, Spirulina princeps, Spirulina laxissima, Spirulina curta* and *Spirulina spirulinoides*. Of these, *Spirulina platensis, Spirulina maxima, Spirulina geitleri* and *Spirulina siamese* are preferred between when they can be artificially cultivated and are readily available.

Spirulina exists in a variety of forms, including live spirulina, dry spirulina, and treated spirulina prepared by mechanical treatment or some other type of treatment process.

Live spirulina can be obtained by using methods such as centrifugal separation and filtration to harvest spirulina grown in water. Live spirulina can be used directly in the state in which it has been harvested from the production pond, although it is preferably washed with water or physiological saline.

Examples of dry spirulina include live spirulina obtained by the method described above that has been subsequently freeze dried or spray dried.

Treated spirulina prepared by mechanical treatment or some other type of treatment process include those obtained by subjecting live spirulina to ultrasonication or to mechanical treatment such as homogenization. The treated spirulina may be subsequently subjected to drying treatment.

The spirulina used in the inventive treatment process is preferably live spirulina because it retains more of the active ingredients of spirulina.

Depending on the degree to which water has been removed during harvesting, the live spirulina is generally in the form of a suspension in water, a paste having a lower water content than a suspension, or a cake having a lower water content than a paste. Spirulina can be used in any of these forms, although it is preferable to use spirulina that has been rendered into the form of a suspension. If dry spirulina or treated spirulina is used in the inventive process, the spirulina may be used in the dried state or water may be added so as to render it into the form of a suspension, paste or cake as in the case of live spirulina.

To avoid a loss of the active ingredients in spirulina, the spirulina used in this invention is one that has not been previously heat-sterilized. Spirulina contains components that have health-maintaining and promoting effects, including phycocyanin, which is known to have anti-inflammatory and liver-protecting actions, and chlorophyll, which is known to have bactericidal, anti-allergy, metabolism-promoting, cancer preventing, blood-cleansing and hematopoietic system-activating effects. Heat-sterilization destroys these active ingredients.

Next, the lactic acid bacteria are described. Lactic acid bacteria have been used since ancient times in the processing of many types of foods, including fermented dairy products, brewed beverages and pickled vegetables and fruit, for the purpose of preserving and flavoring foods. Lactic acid bacteria and their metabolites also have many desirable physiological effects, including bowel-regulating, blood cholesterol-lowering and blood pressure-lowering actions, and are thus used also as food products for promoting health.

Any edible lactic acid bacteria may be employed without limitation as the lactic acid bacteria in the present invention. Lactic acid bacteria are classified according to the growth environment from which they come, and include milk lactic acid bacteria, plant-associated lactic acid bacteria, intestinal lactic acid bacteria and lactic acid bacteria which originate in the natural salt lakes where spirulina grows. Lactic acid bacteria are also classified according to the conditions optimal for the growth of lactic acid bacteria as mesophilic bacteria, thermophilic bacteria and halotolerant bacteria. Lactic acid bacteria having any of these qualities may be used.

The lactic acid bacteria used in the invention are exemplified by, taxonomically, bacteria belonging to the genera *Lactobacillus, Pediococcus, Tetragenococcus, Carnobacterium, Vagococcus, Leuconostoc, Weissella, Oenococcus, Atopobium, Streptococcus, Enterococcus, Lactococcus, Aerococcus, Alloiococcus, Melissococcus* and *Bifidobacterium*. Exemplary species include *Lactobacillus delbrueckii, Lactobacillus plantarum, Lactobacillus acidophilus, Lactococcus lactis* and *Leuconostoc* sp. Lactic acid bacteria of the genus *Pediococcus* are preferred because they are able to reduce the characteristic odor and taste of spirulina.

A single species of lactic acid bacteria may be used alone, or two or more species may be used in admixture. Moreover, as described subsequently, in the step in which the lactic acid bacteria are cultured within spirulina, a single type of bacteria may be divided up and inoculated in two or more stages, or different types of bacteria may be inoculated and grown in the spirulina.

The lactic acid bacteria used may be ones that have been grown on an agar medium or a liquid medium, then preserved such as by refrigeration, freezing or drying. It is preferable for these preserved lactic acid bacteria to be a culture prepared by inoculation in a liquid medium and cultivation (abbreviated below as "seed culture") because the lactic acid bacteria have a rapid growth rate and high activities, including the ability to produce flavors (e.g., acetaldehyde, diacetyl) and the ability to produce organic acids. No particular limitation is imposed on the medium used for cultivating the seed culture, provided it is a medium capable of supporting growth of the lactic acid bacteria to be used. Examples of liquid media in which lactic acid bacteria are generally cultivated include the MRS medium devised by Man, Rogosa and Sharpe (available from Merck), whey media which contain milk components, and nonfat milk media. To prevent the entry of other foreign matter into the medium used for preparing the seed culture, use can be made of a medium to which has been added heat-sterilized enzyme degradation products of spirulina, acid or alkali degradation products of spirulina, and sugars such as glucose or amino acids. Preparation of the seed culture generally involves adding preserved lactic acid bacteria to the liquid medium described above, maintaining the medium in an aerobic or anaerobic state suitable for the lactic acid bacteria being cultivated, and carrying out 8 to 36 hours of standing or stirred culture at 20 to 40° C.

Next, the treatment process of the invention is described. No particular limitation is imposed on the inventive treatment process, provided it is a process in which a mixture composed of spirulina and lactic acid bacteria is kept in the presence of water and the lactic acid bacteria in the mixture are cultured. Keeping the mixture in the presence of water may involve keeping a mixture of spirulina and lactic acid bacteria in water or keeping a mixture of spirulina and lactic acid bacteria in a wet state, although keeping the mixture in water is preferred. Methods for keeping a mixture of spirulina and lactic acid bacteria in the presence of water include:

(1) adding a liquid culture of lactic acid bacteria or dried lactic acid bacteria to a suspension or paste of live spirulina or dried spirulina;

(2) adding a liquid culture of lactic acid bacteria to a cake of live spirulina or dried spirulina; and (3) adding a liquid culture of lactic acid bacteria to dried spirulina in an amount sufficient to place the spirulina in a wet state.

Of these, method (1) is preferred. Moreover, in method (1), to provide a high ability to cultivate lactic acid bacteria and a high ability to produce flavor, it is preferable for the spirulina to be a suspension of live spirulina and for the lactic acid bacteria to be a liquid culture, and especially a seed culture.

The spirulina suspension, paste or cake and the lactic acid bacteria culture used in the above method contain water, and the mixture of spirulina and lactic acid bacteria is kept in the presence of water. However, if the amount of water is insufficient, water may be added to the mixture and the mixture placed in a state where it is kept wet or in water. The water used is preferably sterilized water.

For a good efficiency in the subsequently described harvesting and drying steps after culturing of the lactic acid bacteria, the spirulina content when the mixture of spirulina and lactic acid bacteria has been maintained in the presence of water is preferably 0.1 to 30 parts by weight, and more preferably 1 to 20 parts by weight, per 100 parts by weight of spirulina, lactic acid bacteria and water combined.

The culturing operation in which the mixture of spirulina and lactic acid bacteria are kept in the presence of water and the lactic acid bacteria are cultured may be carried out as a standing culture or, if the mixture when kept in the presence of water is in the state of a liquid, as a stirred culture using a propeller. The mixture being cultured may be placed in an anaerobic state or an aerobic state as appropriate for growing the particular type of lactic acid bacteria being used.

The amount of lactic acid bacteria used need only be a number of lactic acid bacteria cells that will propagate. However, to successfully inhibit the propagation of foreign bacteria, it is preferable for the number of lactic acid bacteria at the start of lactic acid bacteria cultivation to be from $1 \times 10^5$ to $1 \times 10^{11}$ cells, and preferably from $1 \times 10^6$ to $1 \times 10^9$ cells, per gram of spirulina (solids basis).

The pH when the mixture of spirulina and lactic acid bacteria is kept in the presence of water varies with the stage of cultivation according to acids such as lactic acid that form during lactic acid bacteria cultivation, although the pH at the start of cultivation is preferably 5.0 to 9.0, and more preferably 6.0 to 8.0.

The culturing temperature may be any temperature at which the lactic acid bacteria can grow. However, for good growth of the lactic acid bacteria and to avoid a loss of the active ingredients in spirulina, the culturing temperature is preferably from 4 to 45° C., and more preferably from 20 to 40° C.

The culturing time is preferably 1 to 48 hours, more preferably 3 to 36 hours, and most preferably 8 to 24 hours. To fully suppress the growth of other, foreign bacteria and effectively reduce the taste and odor characteristic of spirulina, it is preferable for the number of lactic acid bacteria following cultivation to increase 10- to 1,000-fold, and preferably by 80- to 300-fold, relative to the number of lactic acid bacteria at the start of cultivation. To maintain an optimal pH for growth of the lactic acid bacteria, the pH may be adjusted by adding a basic compound such as ammonium hydroxide. However, owing to the presence of lactic acid and other substances produced by the lactic acid bacteria, the pH of the spirulina suspension falls to about 4.0, which is desirable for reducing the level of foreign bacteria.

The treatment process of the invention may be any in which a mixture of spirulina and lactic acid bacteria is held in the presence of water and the lactic acid bacteria are cultured. However, a method wherein sugar is also included together with the water so as to culture the lactic acid bacteria while keeping the mixture in the presence of both water and sugar is preferred because the odor and taste characteristic of spirulina can be further reduced and the growth of foreign bacteria can be inhibited. This foreign bacteria growth-inhibiting effect is especially striking when the spirulina used is dry spirulina, which is prone to the propagation of foreign bacteria.

The sugar is exemplified by monosaccharides, oligosaccharides and polysaccharides. Specific monosaccharides include glucose, galactose, mannose, fructose, ribose and xylose. Specific oligosaccharides include disaccharides such as sucrose and maltose, as well as fructooligosaccharide, soybean oligosaccharide, xylooligosaccharide and raffinose. Specific polysaccharides include amylose, amylopectin, cellulose, glycogen, β-glucan and mucopolysaccharide. The sugar is preferably an oligosaccharide, and most preferably galactooligosaccharide.

The method for keeping the mixture of spirulina and lactic acid bacteria in the presence of water and sugar is not subject to any particular limitation. For example, the spirulina, lactic acid bacteria and sugar may be mixed together, spirulina to which the sugar has been added beforehand may be mixed with the lactic acid bacteria, or lactic acid bacteria to which the sugar has been added beforehand may be mixed with the spirulina. It is preferable to use the sugar as a solid, although it may be used in the form of an aqueous solution obtained by dissolving the sugar in water or the like.

The amount of sugar used is preferably 0.5 to 20 parts by weight, more preferably 1 to 15 parts by weight, and most preferably 3 to 10 parts by weight, per 100 parts by weight of the spirulina, lactic acid bacteria and sugar combined.

In the inventive method of preparation, the antibacterial effects of organic acids (e.g., lactic acid, acetic acid) and bacteriocin produced during growth of the lactic acid bacteria reduces the number of other foreign bacteria in the spirulina suspension, making the lactic acid bacteria the dominant species. Moreover, flavors produced by the lactic acid bacteria, such as acetaldehyde and diacetyl, reduce the odor and taste characteristic of spirulina, providing a flavor that lends itself to use in food products. The resulting spirulina or spirulina suspension can be used directly without modification in lactic acid bacteria beverages and lactic acid bacteria-containing foods. The spirulina obtained by the inventive treatment process is preferably used without lowering or eliminating the number of accompanying lactic acid bacteria, although if necessary the number of accompanying lactic acid bacteria can be lowered or eliminated such as by washing.

If necessary, the spirulina obtained by the inventive treatment process can be administered drying treatment or even powdered. Drying treatment is generally carried out to a moisture content in the spirulina of 4 to 7 wt. %, with treatment capable of maintaining the number of lactic acid bacteria being preferred. Examples of preferred drying methods include freeze drying and spray drying, although spray drying is more preferable from the standpoint of cost. During drying treatment, production efficiency increases as the temperature of the exhausted air rises, but to ensure a good spirulina quality and avoid a decrease in the number of lactic acid bacteria, it is desirable to carry out drying at a product temperature in a range of preferably 30 to 70° C., and more preferably 40 to 60° C. "Product temperature," as used herein, refers to the temperature of a specimen.

The spirulina obtained by the inventive treatment process contains few undesirable foreign bacteria such as *E. coli* and has less of the taste and odor characteristic of spirulina. Moreover, the spirulina can be imparted with lactic acid bacteria having useful health-promoting functions, and their metabolites. Hence, such spirulina can be used not only in health foods and specialty feeds, but also in general food products, beverages, and nutritional supplements.

EXAMPLES

Reference examples, working examples of the invention and comparative examples are given below by way of illustration. Unless noted otherwise, all parts and percents in the examples are by weight.

Reference Example 1

Preparation of Lactic Acid Bacteria Seed Culture

Lactic acid bacteria (*Lactobacillus plantarum*) preserved by freezing were inoculated into 10 ml of MRS medium (available from Merck; Catalog No. 10661) and standing cultured at 30° C. for 18 hours to give a seed culture of lactic acid bacteria. This is referred to below as Lactic Acid Bacteria Culture 1.

Reference Examples 2 to 5

Preparation of Lactic Acid Bacteria Seed Cultures

Aside from using *Lactobacillus lactis* in Reference Example 2, *Lactobacillus acidophilus* in Reference Example 3, *Leuconostoc* in Reference Example 4 and *Pediococcus* in Reference Example 5 instead of *Lactobacillus plantarum*, Lactic Acid Bacteria Culture 2, Lactic Acid Bacteria Culture 3, Lactic Acid Bacteria Culture 4 and Lactic Acid Bacteria Culture 5 were prepared in the same way as in Reference Example 1.

Example 1

Spirulina was cultivated and produced in a cultivation pond under 7 days of continuous illumination using artificial light, then harvested. After being harvested, the spirulina was washed with physiological saline, thereby giving 20 g of spirulina (solids content, 20%). This washed spirulina was then suspended in 180 ml of physiological saline to form a suspension. To this suspension was added 10 g of galactooligosaccharide, in addition to which the Lactic Acid Bacteria Culture 1 prepared in Reference Example 1 was inoculated into the suspension in an amount of $5 \times 10^8$ lactic acid bacteria per gram of spirulina dry weight. The concentration was adjusted to a pH of 7.0 with a 0.1 mol/L sodium hydroxide solution, following which the lactic acid bacteria were shake-cultured at 30° C. for 24 hours. The resulting liquid culture was then fed to a small spray dryer and spray-dried at a product temperature of 55° C., giving a spirulina powder. This is referred to below as "Spirulina Powder 1."

Examples 2 to 5

Aside from using Lactic Acid Bacteria Culture 2 in Working Example 2, Lactic Acid Bacteria Culture 3 in Working Example 3, Lactic Acid Bacteria Culture 4 in Working Example 4, and Lactic Acid Bacteria Culture 5 in Working Example 5 instead of Lactic Acid Bacteria Culture 1, Spirulina Powders 2 to 5 were each prepared in the same way as in Working Example 1. In Working Examples 1 to 5, the number of lactic acid bacteria after cultivation increased 10 to 80-fold relative to the number of lactic acid bacteria at the start of cultivation.

Example 6

Ten grams of spirulina dry powder was suspended in 190 ml of physiological saline, thereby forming a suspension. To this suspension was added 10 g of galactooligosaccharide, after which the suspension was inoculated with the Lactic Acid Bacteria Culture 1 prepared in Reference Example 1 such as to set the number of lactic acid bacteria to $2 \times 10^8$ per gram of spirulina. The pH was adjusted to 7.0 with a sodium hydroxide solution having a concentration of 0.1 mol/L, following which a standing culture of the lactic acid bacteria was carried out at 30° C. for 24 hours. The resulting liquid culture was fed to a small spray dryer and spray drying was carried out at a product temperature of 55° C., giving a spirulina powder. This is referred to below as "Spirulina Powder 6."

Examples 7 to 10

Aside from using Lactic Acid Bacteria Culture 2 in Working Example 7, Lactic Acid Bacteria Culture 3 in Working Example 8, Lactic Acid Bacteria Culture 4 in Working Example 9, and Lactic Acid Bacteria Culture 5 in Working Example 10 instead of Lactic Acid Bacteria Culture 1, Spirulina Powders 7 to 10 were each prepared in the same way as in Working Example 6. In Working Examples 6 to 10, the number of lactic acid bacteria after cultivation increased 50 to 200-fold relative to the number of lactic acid bacteria at the start of cultivation.

Comparative Example 1

Spirulina was cultivated and produced in a cultivation pond under 7 days of continuous illumination using artificial light, then harvested. After being harvested, the spirulina was washed with physiological saline, then 20 g of spirulina (solids content, 20%) was suspended in 180 ml of physiological saline, thereby forming a suspension. The suspension was then fed to a small spray dryer and spray drying was carried out at a product temperature of 55° C., giving a spirulina powder for use as a control. This is referred to below as "Spirulina Powder A."

Tests 1 to 10, and Comparative Test 1

The cell count of bacteria other than lactic acid bacteria (abbreviated below as "general live cell count") in Spirulina Powders 1 to 10 and Spirulina Powder A was measured, and the taste and odor were evaluated by sensory testing. The results are shown in Table 1. Cell count determinations and sensory tests were carried out as described below. Sensory tests were performed using a ten-person panel.

Standard Plate Count

A suspension was prepared by suspending 1.0 g of spirulina powder in 19 ml of phosphate buffer physiological saline. Using the phosphate buffer physiological saline, the suspension was further diluted one-fold, 10-fold, $10^2$-fold, $10^3$-fold and $10^4$-fold.

One milliliter of each of the sample dilutions was mixed with 10 ml of an ordinary bouillon agar medium (produced by Kyokuto Pharmaceutical Industrial Co., Ltd.; Code No. 02480) on a Petri dish, solidified, then cultured at 35° C. for 48 hours. Using an agar medium confirmed to have 30 to 300 colonies of general growth bacteria, the colony count on the agar medium was determined. This count was multiplied by the dilution factor, and the resulting number was regarded as the colony count for general growth bacteria.

Evaluation of Taste

Spirulina Powder 1' was used as the standard. In each case, 0.1 g of spirulina powder was placed on the tongue and tasted. The panelist assigned a score to the taste based on the criteria shown below, and the intensity of the taste was determined using formula (1). A lower intensity value indicates that the characteristic spirulina taste is weaker.

+3: characteristic spirulina taste is about the same as that of the standard product
+2: characteristic spirulina taste is weak
+1: characteristic spirulina taste is very weak
0: no characteristic spirulina taste $$\text{Intensity} = (0 \times N_0 + 1 \times N_1 + 2 \times N_2 + 3 \times N_3)/N \quad (1)$$

Here, N is the total number of panelists, $N_0$ is the number of panelists who assigned a score of 0, $N_1$ is the number of panelists who assigned a score of 1, $N_2$ is the number of panelists who assigned a score of 2, and $N_3$ is the number of panelists who assigned a score of 3.

Evaluation of Odor

Spirulina Powder 1' was used as the standard. In each case, 2 g of spirulina powder was placed in a polyethylene bag, the mouth of the bag was closed, and the contents were shaken for 10 seconds, following which the odor within the bag was smelled. The panelist assigned a score to the odor based on the criteria shown below, and the intensity of the odor was determined using above formula (1). A lower intensity value indicates that the characteristic spirulina odor is weaker.

+3: characteristic spirulina odor is about the same as standard product
+2: characteristic spirulina odor is weak
+1: characteristic spirulina odor is very weak
0: no characteristic spirulina odor

TABLE 1

| | Spirulina Powder No. | Lactic Acid Bacteria Culture No. | Standard plate count (n/g) | Taste | Odor |
|---|---|---|---|---|---|
| Test 1 | 1 | 1 | 0 | +0.3 | +0.3 |
| Test 2 | 2 | 2 | 0 | +0.4 | +0.3 |
| Test 3 | 3 | 3 | 0 | +0.4 | +0.3 |
| Test 4 | 4 | 4 | 0 | +0.3 | +0.3 |
| Test 5 | 5 | 5 | 0 | +0.2 | +0.2 |
| Test 6 | 6 | 1 | 0 | +0.8 | +0.7 |
| Test 7 | 7 | 2 | 0 | +0.7 | +0.7 |
| Test 8 | 8 | 3 | 0 | +0.7 | +0.7 |
| Test 9 | 9 | 4 | 0 | +0.7 | +0.6 |
| Test 10 | 10 | 5 | 0 | +0.4 | +0.5 |
| Comparative Test 1 | A | no | $4.0 \times 10^4$ | +3.0 | +3.0 |

Comparative Example 2

No Addition of Galactooligosaccharide

A suspension was prepared by suspending 10 g of spirulina dry powder in 190 ml of physiological saline. The suspension was inoculated with an amount of the Lactic Acid Culture 1 prepared in Reference Example 1 corresponding to $2 \times 10^8$ cells of lactic acid bacteria per gram of spirulina. The pH was adjusted to 7.0 with a 0.1 mol/L sodium hydroxide solution, and the lactic acid bacteria were standing cultured for 24 hours at 30° C. The resulting liquid culture was fed to a small spray dryer and spray dried at a product temperature of 55° C.; thereby giving a spirulina powder. This is referred to below as "Spirulina Powder B."

Comparative Examples 3 to 5

No Addition of Galactooligosaccharide

Aside from using Lactic Acid Bacteria Culture 2 in Comparative Example 3, Lactic Acid Bacteria Culture 3 in Comparative Example 4 and Lactic Acid Bacteria Culture 4 in Comparative Example 5 instead of Lactic Acid Bacteria Culture 1, Spirulina Powders C to E were each prepared in the same way as in Comparative Example 2. Odor and taste evaluations were carried out in the same way as in Working Examples 1 to 10. The results are shown in Table 2.

Comparative Tests 2 to 5

Cell counts for lactic acid bacteria and for other bacteria (the cell count of other bacteria being abbreviated below as "general live cell count") were measured for Spirulina Powders B to E obtained in Comparative Examples 2 to 5, in addition to which the taste and odor were evaluated by sensory testing. The results are shown in Table 2. The same methods were used to evaluate taste and odor as in Tests 1 to 10. Similar evaluations were carried out on the spirulina dry powder used as the starting material in Comparative Example 2 (Comparative Test 6).

TABLE 2

| | Spirulina Powder No. | Lactic Acid Bacteria Culture No. | Sugar | Standard plate count (n/g) | Taste | Odor |
|---|---|---|---|---|---|---|
| Comparative Test 2 | B | 1 | none | $2.0 \times 10^2$ | +0.8 | +0.6 |
| Comparative Test 3 | C | 2 | none | $3.0 \times 10^2$ | +0.9 | +0.9 |
| Comparative Test 4 | D | 3 | none | $8.0 \times 10^3$ | +1.2 | +1.2 |
| Comparative Test 5 | E | 4 | none | $1.0 \times 10^3$ | +1.1 | +1.2 |
| Comparative Test 6 | bulk powder | none | none | $4.0 \times 10^4$ | +3.0 | +3.0 |

It is apparent from this comparative examples and from Working Examples 1 to 10 that the addition of sugar acts to suppress the growth of general live cells.

Comparative Examples 6 and 7

In these examples, the general live cell count was determined in the same way as in Working Example 1 for chlorella powder that was not high-temperature sterilized (Comparative Example 6), and for chlorella powder that was likewise not high-temperature sterilized and was obtained by growing lactic acid bacteria in the same way as in Example 6 but without the addition of sugar, specifically galactooligosaccharide (Comparative Example 7). The results are shown in Table 3.

TABLE 3

| | Standard plate count (n/g) |
|---|---|
| Comparative Example 6 | $2.0 \times 10^4$ |
| Comparative Example 7 | $3.0 \times 10^2$ |

It is apparent from these comparative examples that when lactic acid bacteria are grown without sterilizing the chlorella under applied heat, the general live cell count is high.

Comparative Example 8

The amount of phycocyanin was measured in Spirulina Powder F (Comparative Example 8) obtained by using a high temperature-sterilized spirulina powder, adding sugar (galactooligosaccharide) and cultivating, in Spirulina Powder 6 obtained in Working Example 6 (using spirulina powder that was not high-temperature sterilized), and in the starting spirulina powder that was not high-temperature sterilized.

Spirulina Powder F was produced as follows. Ten parts of spirulina dry powder was suspended in 190 parts of physiological saline and the suspension was sterilized for about 3 seconds at about 130° C., following which the suspension was immediately and rapidly cooled to room temperature. This suspension was subsequently used to prepare spirulina powder in the same way as in Working Example 6. The resulting product is referred to below as "Spirulina Powder F."

The amount of phycocyanin was analyzed by the method of the Japan Health Food & Nutrition Food Association. That is, 0.5 g of spirulina powder was added to 25 ml of a 0.1 M sodium phosphate buffer (pH 6), suspended, and extracted. The extract was then centrifugally separated, and subsequently filtered using filter paper, giving a supernatant. Next, 2 ml of the supernatant was diluted with water up to 50 ml, and the absorbances at wavelengths of 560 nm, 618 nm and 650 nm were measured with a spectrophotometer. The amount of phycocyanin was determined using the following formula.

$$\text{Amount of phycocyanin (\%)} = [(0.198 \times A_{618} - 0.0019 \times A_{560} - 0.133 \times A_{650}) \times D \times 100]/W$$

Here, $A_{560}$ is the absorbance at 560 nm, $A_{618}$ is the absorbance at 618 nm, $A_{650}$ nm is the absorbance at 650 nm, D is the degree of dilution (in this case, 25×25=625), and W is the sample weight (mg).

TABLE 4

| | Spirulina Powder No. | Amount of phycocyanin (%) |
|---|---|---|
| Comparative Example 8 | F | 0.8 |
| Working Example 6 | 6 | 7.8 |
| | bulk powder | 9.0 |

This comparative example demonstrates that spirulina powder cultivated from spirulina which has been high-temperature sterilized contains a much smaller amount of phycocyanin than spirulina powder obtained according to the inventive treatment process.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A process for treating Spirulina in order to reduce the odor and the taste which is characteristic of Spirulina, comprising:
    placing Spirulina that has not been previously heat-sterilized in water to form a suspension,
    inoculating the suspension with a culture of lactic acid bacteria,
    adding a sugar to the suspension,
    culturing the lactic acid bacteria by incubating the suspension to make a liquid culture, and
    drying the resulting liquid culture to produce a dried Spirulina product with reduced odor and taste,
    wherein the Spirulina placed in water is in an amount of 1 to 20 parts by dry weight per 100 parts of the combined weight of the Spirulina, lactic acid bacteria, sugar and water.

2. The process of claim 1, wherein the number of the lactic acid bacteria at the start of the culturing is from $1 \times 10^6$ to $1 \times 10^9$ cells per gram of the dry weight of Spirulina.

3. The process of claim 2, wherein the lactic acid bacteria are cultured at a pH of 6 to 8 and incubated for a time period of 8 to 24 hours.

4. The process of claim 1, wherein the Spirulina placed in water is in the form of a powder.

5. The process of claim 1, wherein the Spirulina placed in water is a live Spirulina.

6. The process of claim 1, wherein the lactic acid bacteria belong to the genus *Pediococcus*.

7. The process of claim 1, wherein the lactic acid bacteria belong to the genus *Lactobacillus*.

8. The process of claim 1, wherein the sugar is in an amount of 0.5 to 20 parts by weight per 100 parts of the combined weight of the Spirulina, lactic acid bacteria, sugar and water.

9. The process of claim 1, wherein the sugar is a galactooligosaccharide.

10. The process of claim 1, wherein the resulting liquid culture is spray dried.

* * * * *